(12) United States Patent
Björk

(10) Patent No.: US 6,961,127 B2
(45) Date of Patent: Nov. 1, 2005

(54) DEVICE AND METHOD FOR OPTICAL INSPECTION

(75) Inventor: Svante Björk, Kungsbacka (SE)

(73) Assignee: Svante Bjork AB (SE)

( * ) Notice: Subject to any disclaimer, the term of this patent is extended or adjusted under 35 U.S.C. 154(b) by 538 days.

(21) Appl. No.: 10/125,590

(22) Filed: Apr. 19, 2002

(65) Prior Publication Data

US 2002/0154307 A1 Oct. 24, 2002

(30) Foreign Application Priority Data

Apr. 19, 2001 (SE) .............................................. 0101374

(51) Int. Cl.⁷ .............................................. G01N 21/84
(52) U.S. Cl. ..................... 356/430; 356/431; 356/239.7; 356/237.2
(58) Field of Search ......................... 356/429, 430–431, 356/237.1, 237.2, 237.3, 238.1, 238.2, 238.3, 239.1, 239.7, 239.8; 382/141, 144, 145, 147, 149

(56) References Cited

U.S. PATENT DOCUMENTS

| | | | |
|---|---|---|---|
| 4,417,149 A | 11/1983 | Takeuchi et al. | ............ 250/563 |
| 5,068,799 A | 11/1991 | Jarrett, Jr. | .................... 364/507 |

FOREIGN PATENT DOCUMENTS

| | | | | |
|---|---|---|---|---|
| EP | 0543629 A1 | 11/1992 | .......... | G01N/21/89 |
| EP | 0696733 A1 | 2/1996 | .......... | G01N/21/89 |
| GB | 2224831 A | * 5/1990 | .......... | G06F/15/70 |
| JP | 07190956 | * 12/1993 | .......... | G01N/21/89 |
| SE | 9801170-3 | 4/1998 | .......... | G01N/21/84 |
| SE | 511822 | 11/1999 | .......... | G01N/21/89 |
| SE | 514081 | 12/2000 | .......... | G01B/11/30 |
| SE | 514090 | 12/2000 | .......... | G01N/21/89 |
| WO | WO 98/21568 | 5/1998 | .......... | G01N/21/89 |
| WO | WO 99/51969 A1 | 10/1999 | .......... | G01N/21/84 |

* cited by examiner

*Primary Examiner*—Gregory J. Toatley, Jr.
*Assistant Examiner*—Roy M. Punnoose
(74) *Attorney, Agent, or Firm*—Lacasse & Associates, LLC; Randy W. Lacasse; Ramraj Soundararajan

(57) ABSTRACT

The invention relates to a method for optical inspection with a scanner which is arranged for detection and measurement of defects in or on a material which is inspected. The inspection takes place in successive sweeps essentially in the transverse direction of the material, with each respective sweep corresponding to a plurality of pixels in said scanner. The invention is characterized in that it comprises a rolling buffer storing at least one sweep which precedes another sweep in which at least one pixel indicates triggering corresponding to a detected defect in the material. The invention also relates to a device for such inspection. By means of the invention, an improved measurement accuracy is obtained when detecting defects using the measurement system described.

30 Claims, 2 Drawing Sheets

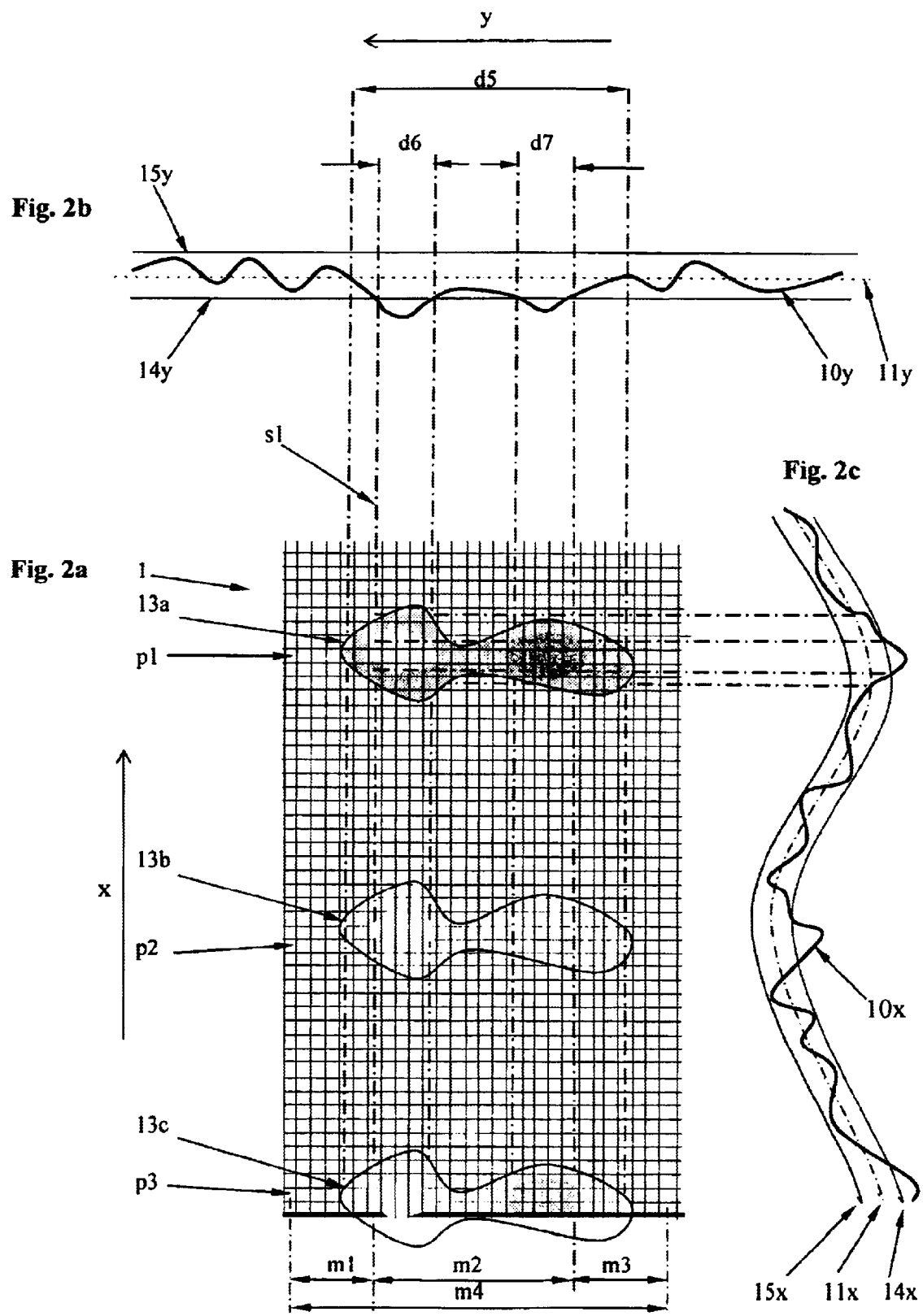

DEVICE AND METHOD FOR OPTICAL INSPECTION

This application claims priority under 35 U.S.C. 119 of Swedish patent application no. 0101374-7, filed Apr. 19, 2001, which is hereby incorporated by reference in its entirety and for all purposes.

FIELD OF INVENTION

The present invention relates to the field of optical inspection. More specifically, the present invention relates to a method and system for optical inspection using a scanner for detecting and measuring defects in or on a material being inspected.

BACKGROUND ART

When producing transparent materials such as, for example, polyethylene or polypropylene materials, it is extremely important that the material contains as few pollutants as possible. For this reason, it is previously known to carry out an optically based inspection of a film or a tape which is produced in the material in question, by means of which any possibly occurring pollutants can be detected.

A measurement system for such a type of inspection or measurement can, for example, comprise equipment with a CCD-scanner, which interacts with a suitable light source for inspection of the material in question.

For example, there can in the above-mentioned materials occur undesired pollutants in the form of non-homogeneities. These non-homogeneities can, for example, consist of oxidized material, foreign particles or so-called gels, which as such are transparent, but which have optical properties which deviate from the rest of the material. This can be detected by means of the above-mentioned equipment for optical inspection.

During optical inspection, defects can be detected by comparing the light transmission in each point with a predetermined threshold or the change compared to a previously stored reference value. If the measured light transmission exceeds or falls below this threshold, this is an indication of the occurrence of a defect in the current inspection point. This corresponds to a "triggering", or "trig".

During optical inspection according to prior art, the tape is inspected in successive sweeps or inspection lines, which normally run crosswise to the longitudinal direction of the tape, which is below referred to as the "y-direction". The transversal direction with reference to the tape is below referred to as the "x-direction". Each and every one of the sweeps will then generate information regarding the light transmission in each respective pixel. This information can then successively be transferred, and stored in a computer unit for later analysis.

Since the major part of a tape, which is intended for optical transmission will be free from defects, there is a need to limit the amount of measurement data generated by the CCD-scanner, and in this way sort out the large part of obtained data which thus is not interesting.

In a scanner of a known kind which is used for optical inspection, there is a data reduction by data which is generated at those sweeps which do not obtain a trig signal being discarded or written over. In other words the information regarding those sweeps which do not generate a signal which indicates that the current threshold value for light transmission has been exceeded/fallen below is ignored, which corresponds to a defect not having been found. This is done since there is no interest in a later analysis of measurement data which corresponds to a material without defects. If triggering does occur, the sweep in question is saved in a special buffer memory for later analysis in, for example, a PC. In this way, the amount of data which needs to be analysed by the PC is limited.

The above-mentioned threshold level must be set with a margin from the normal light transmission level which can be considered to correspond to a tape without defects. Due to normally occurring variations in the material and noise and disturbances in the measured signal from the CCD-scanner, the threshold value must thus be set at a sufficient distance from the level at which such disturbances occur. This means that those flanks in the y-direction which occur before and after those sweeps which generate a detection (trig signal) will never be included in the buffer memory, since they are often within the margin which is used between the normal measurement signal and the threshold value. This in turn leads to a risk of erroneous calculation of the size of the defects found, which of course is a problem in connection with determining the form and shape of the defect in the case of optical inspection.

When detecting small or transparent defects in moving lines, the sensitivity is also limited by signal variations in the x-direction which are not present in the y-direction. These signal variations can consist of illumination variations, dirt or dust on the optical components of the system, longitudinal lines, so-called day-lines, which occur when producing the tape/film which is to be examined, unevenness in the various pixels of the CCD-camera etc. The optical signal from these signal variations in the x-direction can even exceed the signal from those defects which are to be detected for further analysis.

If the variation of the signal level in the x-direction is used during detection, as is the case of the prior art, it is not possible to detect defects which are present at the start of the x sweep.

SUMMARY OF THE INVENTION

The invention relates to an improved method for optical inspection using a scanner which is arranged for detecting and measuring defects in or on a material which is being inspected. The inspection takes place in successive sweeps essentially in the transverse direction of the material, with the respective sweep corresponding to a plurality of pixels of said scanner. A rolling buffer stores at least one sweep which precedes another sweep in which at least one pixel indicates triggering corresponding to a detected defect in the material.

The invention also relates to a device for optical inspection comprising a scanner which is arranged for detection and measurement of defects in or on a material which is inspected. The inspection takes place in successive sweeps essentially in the transverse direction of the material, with each respective sweep corresponding to a plurality of pixels in said scanner. The device comprises a central computer unit with a memory unit, with the computer unit or the memory unit further comprising a rolling buffer storing at least one sweep which precedes another sweep in which at least one pixel indicates triggering corresponding to a detected defect in the material.

DESCRIPTION OF THE FIGURES

The invention will be described with reference to an example of preferred embodiment and the appended drawings, in which:

FIG. 2a shows a depiction of three similar defects positioned in various x-positions with a varying signal level in the x-direction, of which one defect is positioned partially outside of the beginning of the sweep, FIG. 2b shows a curve of the signal variation in the y-direction (along the tape from pixel p1), and how these vary as a consequence of noise, and the defect 13a in FIG. 2a (p2 and p3 are the same since the three defects are the same), and the average value of previous sweeps without detection over time for each respective pixel in the x-direction 11y, and FIG. 2c shows a curve of the signal variation in the x-direction (across the tape in the sweep s1), and how this varies as a consequence of the signal variations 10x in the x-direction, noise and defects 13 a–c in FIG. 2a.

PREFERRED EMBODIMENT

Figure 1:
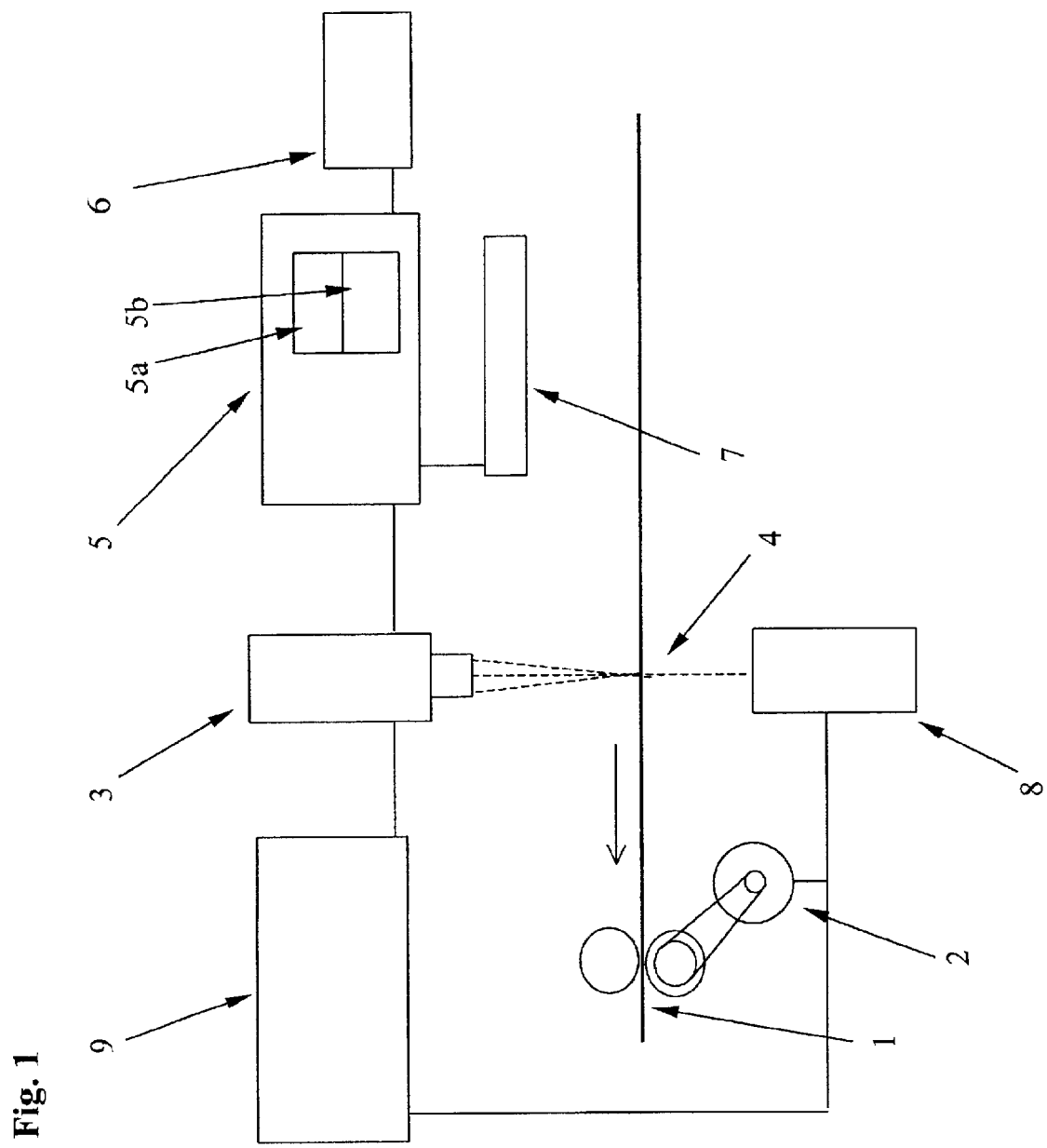
FIG. 1 shows a kind of equipment which is suitable for optical inspection of surface defects on a transparent material.

FIG. 1 schematically shows an equipment for optical detection of defects in a film or tape-shaped material 1, for example an extruded transparent poly-ethylene material. Such defects may be in the order of size of 5–500 μm. By means of the driving device 2, the material 1 is transported through the field of vision 4 of a scanner 3, with the scanner 3 detecting defects in the material. The defects can consist of inhomogeneities in the material or particles alien to the material, for example metal, fiber, soot, gels etc.

The equipment additionally comprises a computer 5 for collecting and processing the measured values. The computer 5 in turn comprises an image memory 5a and a buffer memory 5b, the function of which will be described in detail below. A printer 6 for printing the results of the measurements and a keyboard 7 for entering calibration values etc. In addition, the equipment has a light source 8 for illuminating the object to be measured and an electronic unit 9 for supplying current and controlling the various units.

During measurement, the material 1 will be moved relative to the scanner 3 in the longitudinal direction 1 of the material, which here will be referred to as the y-direction. During this relative movement, the scanner 3 will sweep across the material, i.e. in its x-direction, in consecutive inspection lines (or "sweeps") and will for each pixel detect a measured value regarding the transmission of light.

In FIG. 2b there is shown a possible sequence during optical inspection according to the invention in which the light value from the material is detected. The light value over time (y-direction) for a certain pixel in the x-direction, for example p1, is then shown with a curve marked with the reference numeral 10y. When a defect has been found, the light transmission is altered, and deviates from the normal noise level, and can exceed or fall below predetermined limits (triggering levels), which are marked with the reference numerals 14y and 15y, respectively. These limit levels 14y, 15y are then set with a margin to the expected normal light variation of the rest of the material, since it can be expected that a certain amount of noise and other disturbances will cause the signal variation for the not defected portions to vary to a certain extent.

According to what can be seen in FIG. 2b, there is thus a lowering of the signal level below a lower limit level 14y. According to prior art, it can be said that this defect is detected as two defects of lengths d6 and d7 in FIG. 2b. This measurement of the dimensions of the defect will, however, not give a correct result, since the values measured in the flanks of the curve can also be said to be of importance when the dimensions and properties of the rest of the curve are to be evaluated. It can, for example, then be said that the true signal attenuation which the defect has caused should be calculated starting from the order of size which is indicated with the reference numeral d5 in FIG. 2b.

With the intention of including information in the flanks of the curve 10y when determining the nature and dimensions of the defect, it is a principle behind the invention to save a rolling buffer memory 5b comprising a predetermined amount of sweeps in the y-direction. As new sweeps are added without any trig being generated, this buffer will gradually be written over with new sweeps. This buffer, which is indicated in FIG. 1 with the reference numeral 5b, and which below will be referred to as a pre-sweep buffer, comprises one or several sweeps which later will precede the sweep in which the trig is indicated. The pre-sweep buffer 5b can suitably comprise, for example, seven sweeps, i.e. information regarding the light transmission in each pixel along seven inspection lines in the x-direction which are before the sweep in which a triggering has occurred.

The principle behind the invention will also become evident from FIGS. 2a and 2c, which in principle show how a portion of a material 1 is inspected. During movement of the material 1 relative to a scanner (not shown in FIGS. 2a–c), there is an inspection, sweep for sweep, in the x-direction of the material 1. Those portions of the material which are inspected and which correspond to light sensitive pixels in the scanner are shown as squares in the material 1 in FIG. 2a. Also shown schematically are three defects 13a–c, with shadowed areas over those squares which correspond to the light-sensitive elements of the CCD-scanner. Parts of these defects thus correspond to an amount of pixels in which the light transmission is lower than the threshold value, which is indicated with the reference numeral 14y in FIG. 2b, while other parts of the defect are higher than the threshold values indicated as 14y.

When a trig has occurred in a sweep, the information in the pre-sweep buffer is moved, together with the sweep in which the detection occurred, to the so-called image memory 5a (see FIG. 1), following which the image memory is filled with new sweeps as long as the sweeps contain a detection (trig). When the trig condition is no longer fulfilled, the writing in the image memory will continue with information from an additional seven sweeps (post-sweeps), which are indicated with the reference numeral m3 in FIG. 2a. If a trig occurs during storage of the post-sweeps, the countdown of the post-sweeps stops, and the image memory is filled until the trig condition again stops, following which the storage of post-sweeps is restarted.

The image memory will now contain pre-sweep m1, the trig-sweep m2 (and any possible extra pre/post-sweeps) and post-sweep m3, i.e. not just information regarding that which is detected, but also information regarding the defect outside of the area which it has been possible to detect both in the x- and the y-directions (m4 times for example 2048 pixel values). After this, the storage of new information reverts to the pre-sweep buffer, and the sequence can start again.

According to the invention above, there is now in the image memory 5a not just that part of the defect which it has been possible to detect since it has been trigged relative to the threshold values 14y, 15y, but also the area around this triggering area in both the x- and y-directions. The total area thus comprises the flanks, which according to prior art have been lost. In this way, the entire defect 13a–c together with its environs can be analysed subsequently by the computer 5.

If a new defect in another place in the sweep is detected before the first defect has passed, the buffer memory continues to be filled until triggering ceases, following which post-sweeps are stored in the buffer memory.

The size of the image memory 5a can be chosen to contain a number of sweeps which in turn corresponds to the number of defects which can be expected to occur during a measurement occasion, or the time which is necessary for the personal computer to be able to analyse the defects.

During a normal application, a scanner 3 is used which measures with a speed of 10 to 20 million pixels/sec., i.e. 5–10000 sweeps/sec., with the scanner then comprising 2048 pixels. The computer thus only needs to analyse the area where there are pollutions, which in a normal application makes the total data reduction in the order of size of 1:10000. This means that a computer which is used for analysing measured defects can be a special or standard type of data processor of the PC type, which then will be sufficiently quick to handle this limited amount of data.

According to a preferred embodiment, there is in the image memory also stored data regarding where along each sweep (in the x-direction) the triggering has occurred. Since it will then be known where on the sweep the defect 13a–c are located, the PC only needs to analyse the area around the defect, and thus not the entire sweep. This will contribute to a further data reduction, thus making the total data reduction into 1:100000. The data reduction which is obtained in each separate case is dependent upon, for example, the purity of the material which is measured.

Additionally, the invention is preferably designed so that data is stored in the image memory regarding where in the longitudinal direction (y-direction) of the material 1 that the triggering has occurred. Since it will then be known where along the material 1 that the scanner 3 read the information, the PC can calculate where the defect is to be found in both the x- and y-directions, and calculate the size of the pollution in both the x- and y-directions. By saving the position of the defect in the longitudinal direction of the material, the position of the defect can be marked on the material 1, in its longitudinal and/or cross-direction. The marking of the position of a detected defect is, as such, previously known, and the invention can for example be implemented with a system described in the international patent application no. PCT/SE97/01880.

Thus, the above-mentioned computer unit 5 or the memory units 5a and 5b respectively, will contain memory space so that it for each sweep can store the x- and/or y-position for each detection which a defect causes. Suitably, the computer unit 5 or the memory units 5a, 5b will also contain a memory space for each sweep which contains a number of detections which have been detected during one and the same sweep, and another memory space where the detection positions along the x-direction are stored continuously for each sweep.

By saving the position of the defect along the longitudinal direction of the material, a later disposal of those portions of the material which contain defects can be carried out. In addition, this information can be utilized to cut those portions of the material which do not contain defects into small pieces.

The cutting and the sorting out of materials with a detected defect is as such known, for example from the Swedish patent application No. 9901292-4 and will thus not be described in detail here.

In a preferred embodiment, there is also data stored in a reference memory regarding earlier recorded sweeps or an average value of earlier recorded sweeps, so that they can serve as reference values when detecting variations in the y-direction.

Preferably, there is, according to the embodiment, an inspection where the triggering is repeated in a predetermined manner in order to fulfil the triggering condition. For example, the triggering level must be reached at least once, following which it a number of subsequent times exceeds the first one in a certain manner (it can for example be x times larger, where x can be for example 3).

Additionally, the invention preferably comprises a measurement of how much time it will take for the material 1 to be transported a predetermined distance, and a calculation of a distance constant which corresponds to the time between each sweep along the material. Furthermore, there can then be a calculation of the size of the defect in the y-direction starting from said distance constant. So that the resolution (the pulse speed) in the longitudinal sensor will not need to be too great, a longitudinal sensor with low resolution can be chosen if during start of the scanner—i.e. before starting to measure—there is a measurement of the tape speed by measuring how much time (using the clock of the computer) it takes for the tape to move a certain distance (using the longitudinal sensor), for example 1 meter. Following this, the exact distance between each sweep is calculated. This can be done in a very precise manner even using a length sensor with low resolution, if a long measurement distance is chosen, for example 1 meter. The distance constant computed in this way for the time between each sweep can during the measurement be used to calculate the size of the defect in the y-direction with a much higher accuracy than the pixel resolution of the scanner, assuming that the tape speed is not changed during the measurement. The tape speed can, of course, be checked during a measurement, and the distance constant can be adjusted if the speed of the tape has been altered during the measurement.

The invention is not limited to the embodiment shown above, but can be varied within the scope of the claims. For example, the above-mentioned CCD-scanner can be constituted by a laser scanner or some other form of inspection device which is suitable for detecting defects in materials of the above-mentioned kind. Naturally, the size of the image memory and the number of pre- and post-sweeps can be varied depending on the different applications. Furthermore, the information regarding the defect does not need to be moved physically, but can be saved arbitrarily and found again, using so-called data pointers.

According to the embodiment described above, a pre-sweep buffer 5b is used which comprises seven sweeps, and a post-sweep buffer which also comprises seven sweeps. However, the invention is not limited to a specific number of sweeps in the pre-sweep buffer and the post-sweep buffer, but can be implemented with a number of sweeps in the pre- and post-sweep buffers which is adapted to the relevant application. In principle, a number of sweeps ranging from one single sweep to several hundred sweeps can be used in accordance with the present invention. The number of sweeps which is chosen depends for example on the contrast of the defects and the rise time of the system. The invention can also be implemented in a manner so that it uses a pre-sweep buffer but not any post-sweep buffer.

Neither is the invention limited to defects which have been detected by means of an attenuation of the signal, but can also be applied when the defect is detected using a positive signal from defects which focus the light (for example so-called gels) or reflexes and variations in light from incident illumination.

Neither is the invention limited to defects which are detected by means of shining a light through the material, but can also be applied for measuring unevenness of the surface of a tape/film-like material in a way which as such is previously known, for example through the Swedish patent application 9901292-4.

What is claimed is:

1. A method for optical inspection using a scanner which is arranged for detecting and measuring defects in or on a material which is being inspected, with said inspection taking place in successive sweeps essentially in the transverse direction of the material, with the respective sweep corresponding to a plurality of pixels of said scanner, wherein said method comprises:

storing in a rolling buffer at least one sweep which precedes another sweep in which at least one pixel indicates triggering corresponding to a detected defect in the material.

2. The method according to claim 1, wherein the position of the defect in the longitudinal direction of the material is stored and used to indicate the position of the defect on the material in the longitudinal direction of the material.

3. The method according to claim 2, wherein the position of the defect in the transverse direction of the material is stored and used to mark the position of the defect in the material in the transverse direction of the material.

4. The method according to claim 2, wherein the position of the defect in the transverse direction of the material is stored and used for subsequent limitation of an image analysis related to relevant areas of interest along the transverse direction.

5. The method according to claim 2, wherein the position of the defect in the longitudinal direction of the material is stored and later used so that those parts of the material which do not contain defects are cut into smaller portions.

6. The method according to claim 2, said method comprising:

measuring how much time it takes for the material to be transported a predetermined distance, calculating a distance constant which corresponds to time between each sweep along the material, and computing the size in the longitudinal direction of the defect starting from said distance constant.

7. The method according to claim 2, wherein said measurement is carried out on a material which is in a tape- or film-like shape.

8. The method according to claim 2, wherein said material during the measurement is continuously transported so that it passes by said scanner.

9. The method according to claim 2, said method comprising storage of at least one additional sweep after the triggering has ceased.

10. The method according to claim 1, wherein the position of the defect in the transverse direction of the material is stored and used to mark the position of the defect in the material in the transverse direction of the material.

11. The method according to claim 1, wherein the position of the defect in the transverse direction of the material is stored and used for subsequent limitation of an image analysis related to relevant areas of interest along the transverse direction.

12. The method according to claims 1, wherein the position of the defect in the longitudinal direction of the material is stored and later used so that those parts of the material which do not contain defects are cut into smaller portions.

13. The method according to claim 1, wherein triggering occurs in the y-direction of the material by pixel by pixel comparison with earlier read and stored pixels, or average values of earlier read and stored pixels, and at least one predetermined threshold value.

14. The method according to claim 13, wherein said triggering is repeated in a predetermined manner in order for the triggering condition to be fulfilled.

15. The method according to claim 13, wherein measured data from the scanner is erased or written over.

16. The method according to claim 1, wherein triggering occurs in the transverse direction of the material by a pixel for pixel comparison with previously read and stored pixels, or average values of previously read and stored pixels, and at least one predetermined threshold value.

17. The method according to claim 16, wherein said triggering is repeated in a predetermined manner in order for the triggering condition to be fulfilled.

18. The method according to claim 16, wherein measured data from the scanner is erased or written over.

19. The method according to claim 1, wherein said triggering is repeated in a predetermined manner in order for the triggering condition to be fulfilled.

20. The method according to claim 1, wherein measured data from the scanner is erased or written over.

21. The method according to claim 1, said method comprising:

measuring how much time it takes for the material to be transported a predetermined distance, calculating a distance constant which corresponds to time between each sweep along the material, and computing the size in the (longitudinal) direction of the defect starting from said distance constant.

22. The method according to claim 1, wherein said measurement is carried out on a material which is in a tape- or film-like shape.

23. The method according to claim 1, wherein said material during the measurement is continuously transported so that it passes by said scanner.

24. The method according to claim 1, said method comprising storage of at least one additional sweep after the triggering has ceased.

25. A device for optical inspection comprising a scanner which is arranged for detection and measurement of defects in or on a material which is inspected, with said inspection taking place in successive sweeps essentially in the transverse direction of the material, with each respective sweep corresponding to a plurality of pixels in said scanner, said device comprising a central computer unit with a memory unit, with the computer unit or the memory unit further comprising storing at least one sweep which precedes another sweep in which at least one pixel indicates triggering corresponding to a detected defect in the material.

26. The device according to claim 25, wherein the computer unit or the memory unit contains memory space so that for every sweep it can store the transverse and/or the longitudinal position of each detection which a defect causes.

27. The device according to claim 26, wherein the computer unit or the memory unit contains a memory space for each sweep, which contains the number of detections which are detected during one and the same sweep, and another memory space where the detection positions in the transverse direction are stored successively.

28. The device according to claim 26, said computer unit or memory unit being adapted for storing at least one further sweep after the triggering has ceased.

29. The device according to claim 25, wherein the computer unit or the memory unit contains a memory space for each sweep, which contains the number of detections which are detected during one and the same sweep, and another memory space where the detection positions in the transverse direction are stored successively.

30. The device according to claim 25, said computer unit or memory unit being adapted for storing at least one further sweep after the triggering has ceased.

* * * * *